US006245910B1

(12) United States Patent
Izawa et al.

(10) Patent No.: US 6,245,910 B1
(45) Date of Patent: Jun. 12, 2001

(54) PROCESS FOR PRODUCING PURINE DERIVATIVES

(75) Inventors: Kunisuke Izawa; Hiroshi Shiragami; Keizo Yamashita, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/427,989

(22) Filed: Oct. 27, 1999

Related U.S. Application Data

(62) Division of application No. 09/121,117, filed on Jul. 23, 1998, now Pat. No. 6,087,497, which is a division of application No. 08/605,550, filed on Feb. 20, 1996, now Pat. No. 5,831,092.

(30) Foreign Application Priority Data

Feb. 21, 1995 (JP) ................................................ 7-032145
Jan. 25, 1996 (JP) ................................................ 8-010710

(51) Int. Cl.⁷ ..................... C07D 473/30; C07D 473/18; C07D 473/34
(52) U.S. Cl. .................. 544/244; 544/264; 544/265; 544/267; 544/271; 544/272; 544/273; 544/276; 544/277
(58) Field of Search ..................... 544/244, 264, 544/265, 267, 271, 272, 273, 276, 277

(56) References Cited

U.S. PATENT DOCUMENTS 5,336,770   8/1994   Shiragami et al. ................ 544/276
5,942,617   8/1999   Shiragami .......................... 544/276

FOREIGN PATENT DOCUMENTS 0 184 473   6/1986   (EP) .
0 532 878   3/1993   (EP) .
0 664 294   7/1995   (EP) .

OTHER PUBLICATIONS

P. Brookes et al, "The Preparation and Properties of Some Benzylated Nucleosides", *J. Chem. Soc.*, pp. 2026–2028, Aug. 30, 1968.
G. Green et al, "Regiospecific Michael Additions with 2–Aminopurines", *Tetrahedron Letters*, Aug. 4, 1992, pp. 4609–4612, vol. 33, No. 32.
Vel'kina, Chem. Abs. vol. 67, 64362k.
Jones, JACS 84, 1914, 1962.*
Geen, Tet. Letters 33, 4609, 1992.*

* cited by examiner

*Primary Examiner*—Mark L. Berch
(74) *Attorney, Agent, or Firm*—Oblon, Spivak, McClelland, Maier & Neustadt, P.C.

(57) ABSTRACT

Purine derivatives in which a desired substituent is introduced into the 9-position only are synthesized by first introducing an easily-removable substituent in the 7-position of a purine base of natural purine nucleosides obtained through fermentation or derivatives thereof, then hydrolyzing the ribose moiety to form purine derivatives having the substituent in the 7-position, subsequently introducing the desired substituent in the 9-position, and then removing the substituent in the 7-position.

1 Claim, No Drawings

//  PROCESS FOR PRODUCING PURINE DERIVATIVES

This application is a Divisional of U.S. application Ser. No. 09/121,117, filed Jul. 23, 1998, U.S. Pat. No. 6,087,497, which is a Divisional of U.S. application Ser. No. 08/605,550, filed Feb. 20, 1996, now U.S. Pat. No. 5,831,092.

BACKGROUND OF THE INVENTION

1. Field of the Invention

The present invention relates to a process for producing purine derivatives which are useful as medicinal agents which have antiviral activity and antitumor activity. More specifically, the present invention relates to a process for producing purine derivatives selectively by a regioselective addition reaction to the 9-position of 7-benzylpurine derivatives, which can easily be obtained from purine nucleosides or derivatives thereof which are easily produced industrially by fermentation.

2. Description of the Background

Nucleoside derivatives which can be selectively incorporated into a viral DNA or RNA and which exhibit the ability to inhibit the replication of viral DNA or RNA are a group of significant compounds which are useful as agents for treating viral infectious diseases such as herpesvirus, herpes zoster, AIDS, hepatitis, cytomegalovirus and the like because of their selective antiviral activity. Especially useful are purine derivatives which have a substituent in the 9-position. These derivatives include a large number of significant known compounds having antiviral activity such as Acyclovir, Ganciclovir, Famciclovir and the like, and other derivatives under development. Known purine derivatives are shown below.

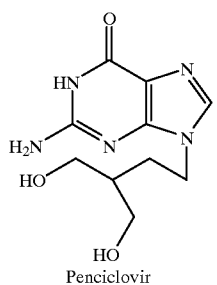
Penciclovir

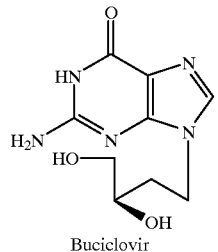
Buciclovir

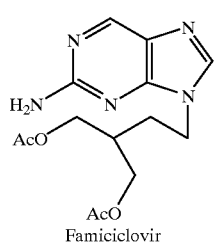
Famciclovir

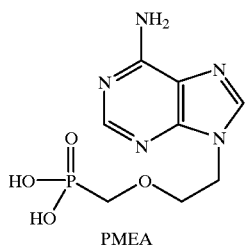
PMEA

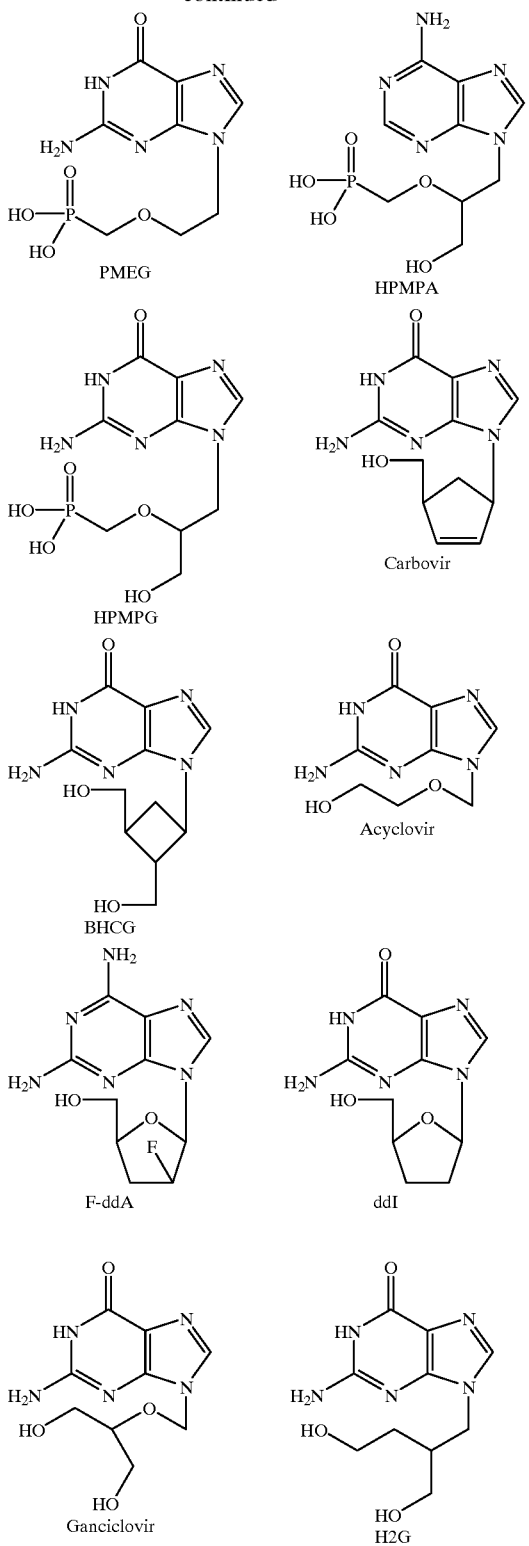

These known purine derivatives are ordinarily synthesized by a method in which a substituent, as a side chain, is added to a purine base. A serious problem of this technique is that it is difficult to introduce a substituent alone at a specific, desired site in the purine base. Many detailed studies have been conducted to solve this problem.

The selectivity for the addition of a substituent at a specific position of the purine base has been studied by a number of investigators. For example, M. Miyaki et al. have reported that when adenine is alkylated, a mixture of substances having substituents in the 3- and 9-positions is obtained (Chem. Pharm. Bull., 18, 1446, 1970). Further, Kjellberg et al have clarified that the selectivity for the 9- or 7-positions upon alkylation varies depending on the difference in the structure between the 1- and 6-positions of guanine derivatives (Nucleosides & Nucleotides, 8, 225, 1989). Still further, Martin et al. have obtained a mixture of substances having substituents in the 9- and 7-positions using diacetylguanine (J. Med. Chem., 26, 759, 1983).

As is apparent from the above-mentioned studies, it is quite difficult to introduce a substituent into the desired position alone of a purine base. When the addition of the substituent occurs in the desired position, but also substitution occurs at another position in the purine base, isomerization has to be conducted after the completion of the addition reaction, or a purification step such as resin treatment or repeated crystallization has to be conducted in order to remove undesired by-product.

For example, when guanine or N-acetylguanine is used as a starting material in the synthesis of the antiviral compound, Penciclovir, the addition of the side chain occurs in two positions, namely, the 9- and 7-positions. Accordingly, an intricate step is required to isolate the intended compound having the substituent in the 9-position, and further the yield thereof is not satisfactory (See Chinese J. of Chem., 9, 536, 1991).

In order to solve this problem, 2-amino-6-chloropurine has been used to improve the selectivity between the 9-position and the 7-position, compared to guanine. However, this method is problematic in that 2-amino-6-chloropurine itself is mutagenic and that the 6-chloro group of the obtained compound has to be hydrolyzed. Further, even if selectivity is improved, it is impossible to completely eliminate the formation of the compound having the side chain in the 7-position. In any case, an intricate purification step is required in this method.

In another study, Graham G. Green et al. have described the synthesis of Famciclovir by a technique in which an iodo substituted side chain is added to 2-amino-6-chloropurine under basic conditions, thereby obtaining a compound having the side chain in the 9-position (75%) and a compound having the side chain in the 7-position (15%). However, the yield of the compound having the side chain in the 9-position is low, while the yield of the compound having the side chain in the 7-position is relatively high. An intricate treatment step is required to remove the latter compound (Tetrahedron Lett. 46(19), 6903, 1990).

Further, Green et al have described a Michael-type addition of a side chain precursor to 2-amino-6-chloropurine, as the purine base, to increase the 9-position:7-position ratio to 40:1. However, in this method, the side chain precursor has to be formed for the Michael-type addition. Consequently, the kind of the substituent is limited, which makes it virtually impossible to add the desired side chain as such. Besides, even though the isomer ratio is raised to 40:1, an intricate treatment step is required to completely remove the small amount of isomer having the side chain in the 7-position (Tetrahedron Lett. 33(32) 4609, 1992).

Harden et al. have synthesized Penciclovir by reacting 2-amino-6-chloropurine with a brominated side chain thereby obtaining the desired compound having the side chain in the 9-position in a yield of 70%, and then hydrolyzing this intermediate. However, the selectivity of this synthesis is not described (Tetrahedron Lett. 26(35), 4265, 1985).

Furthermore, Hannah et al. have reacted 2-amino-6-benzyloxypurine with a side chain tosylate to form a compound having a side chain in the 9-position (17%) and a compound having a side chain in the 7-position (8%) (J. Heterocyclic Chem., 26(5), 1261, 1989).

As stated above, the purine derivatives having the substituent in the 9-position have significant potential as medicinal agents. However, as described above, a significant problem in the art is that a mixture of isomers having side chain substitution at both the 9-position and the 7-position is formed. That is, selective substitution only at the 9-position does not occur. Accordingly, a process in which a substituent is selectively introduced only in the 9-position is in demand.

In considering the state of the art, the present inventors believed that since purine derivatives having a benzyl group in the 7-position can be easily formed from natural purine nucleosides or derivatives thereof which are obtained by fermentation, purine derivatives in which a desired substituent is introduced into the 9-position only can be synthesized by introducing the desired substituent into the 9-position of 7-substituted purine derivatives and subsequently removing the substituent in the 7-position.

A method in which 7-benzylguanine is synthesized by reacting guanosine with benzyl bromide, which results in the substitution of the benzyl group in the 7-position of quanosine, and then treating 7-benzylguanine with an acid is known (P. Brookes et al., J. Chem. Soc. (C) 2026, 1968, and P. K. Bridson et al., Synthetic Commun., 20 (16), 2459, 1990). However, the reaction in which a substituent is reintroduced into the 9-position of 7-benzylguanine has not been reported. Further, Brookes et al disclose that 7-benzylxanthine is also synthesized by reacting 7-benzylguanine produced with sodium nitrite in acetic acid.

By the same method, 7-benzylhypoxanthine can also be obtained from inosine (J. Heterocyclic Chem., 25, 1179, 1988). Further, 7-benzyladenine can be synthesized from adenine in three steps (Synthesis 154, 1988). Thus, a purine base in which the 7-position is protected with the benzyl group can be synthesized by a known method.

There are three known ways in which purine base derivatives protected with a benzyl group are alkylated. That is, in 7-benzylxanthine, alkylation occurs in the 3-position under basic conditions (Synthetic Communications, 20, 2459, 1990). In 7-benzylhypoxanthine, an anion is formed with sodium hydride to cause alkylation in the 1-position (J. Heterocyclic Chem., 25, 1179, 1988). In 3-benzyladenine, alkylation occurs in the 7-position under basic conditions (Chem. Pharm. Bull., 34, 2037, 1986).

As described above, purine derivatives having a substituent in the 7-position can be easily formed. However, an addition reaction in which a substituent is selectively introduced into the 9-position of purine derivatives has not yet been reported.

The present inventors have thoroughly conducted investigations to solve the selectivity problem of the art. It has now been found that an addition reaction proceeds selectively at the 9-position by introducing a benzyl group or a substituted benzyl group in the 7-position of natural purine nucleosides, then hydrolyzing the prepared intermediate by the addition of an acid thereby obtaining 7-benzylpurine derivatives, and reacting the obtained 7-benzylpurine derivatives with a desired substituent to achieve 9-position substitution, and then debenzylating the thus-obtained compounds.

SUMMARY OF THE INVENTION

Accordingly, one object of the present invention is to provide a process by which the 9-position of the purine nucleus can be substituted with high selectivity.

Briefly, this object and other objects of the present invention as hereinafter will become more readily apparent can be attained in a process for producing a compound of formula (3)

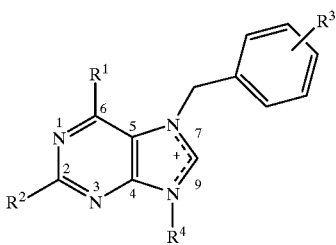

wherein
- $R^1$ is hydrogen, hydroxyl, $C_1-C_8$ saturated or unsaturated lower alkoxy, $C_1-C_8$ saturated or unsaturated lower acyloxy, siloxy, fluoro, chloro, bromo, iodo, amino, $C_1-C_8$ mono- or di-acylamino, alkoxycarbonylamino, allyloxycarbonylamino, or $C_1-C_8$ saturated or unsaturated lower alkyl;
- $R^2$ is hydrogen, hydroxyl, $C_1-C_8$ saturated or unsaturated lower alkoxy, $C_1-C_8$ saturated or unsaturated lower acyloxy, siloxy, fluoro, chloro, bromo, iodo, amino, $C_1-C_9$ mono- or di-acylamino, $C_1-C_8$ alkoxycarbonylamino, allyloxycarbonylamino, or $C_1-C_9$ saturated or unsaturated lower alkyl;
- $R^3$ is hydrogen, $C_1-C_6$ lower alkyl, $C_1-C_6$ lower alkoxy, hydroxyl, nitro, amino, sulfonic acid, carboxyl, $C_1-C_6$ alkoxycarbonyl, fluoro, chloro, bromo, or iodo, and
- $R^4$ is a $C_1-C_{20}$ linear or branched, saturated or unsaturated alkyl, which may have a 3- to 6-membered ring in the molecule and which may have an ether, thioether, acetal, thioacetal, lactone, thiolactone, ketone or amide structure in the molecule; hydroxyl, sulfhydryl, $C_1-C_{20}$ alkoxy, $C_1-C_{10}$ acyl, $C_1-C_{10}$ acyloxy, carboxyl, $C_1-C_{10}$ alkoxycarbonyl, fluoro, amino, phosphoric acid, phosphonic acid, $C_1-C_8$ mono- or di-acylamino, $C_1-C_8$ alkoxycarbonylamino, allyloxycarbonylamino, substituted or unsubstituted phosphoric acid, or substituted or unsubstituted phosphonic acid;

which comprises reacting a 7-benzylpurine derivative represented by formula (1)

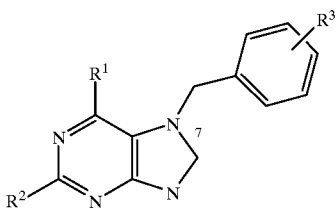

wherein $R^1$, $R^2$ and $R^3$ are as defined above, with a compound having a leaving group represented by formula (2)

$$R^4-X \quad (2)$$

wherein
$R^4$ is as defined above, and
X represents chlorine, bromine, iodine, p-toluenesulfonyloxy, mesyloxy, trifluoromethanesulfonyloxy, alkyl or phenyl carbonate, or $C_1-C_8$ saturated or unsaturated lower acyloxy. When $R^1$ is a hydroxy group in the compounds of formulas (1) and (3), an amide structure of a keto type is stable in the 1-position and the 6-position of the pyrimidine ring.

Another essential embodiment of the present invention is a process for producing 9-substituted purine derivatives represented by formula (4)

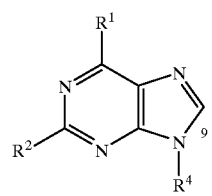

wherein $R^1$, $R^2$ and $R^4$ are as defined above, by reducing the compound of formula (3).

In the present invention, when the compound of formula (1), in which $R^1$ is hydroxyl, $R^2$ is amino, $C_1-C_9$ mono- or di-acylamino, alkoxycarbonylamino, or allyloxycarbonylamino, and when $R^4$ of the compound of formula (2) is represented by formula (5)

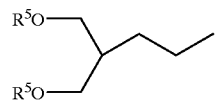

wherein
$R^5$ represents a $C_1-C_9$ acyl group, $C_1-C_{10}$ alkyl group or $C_7-C_{22}$ aralkyl group, the process is especially useful in synthesizing Penciclovir derivatives represented by formula (6)

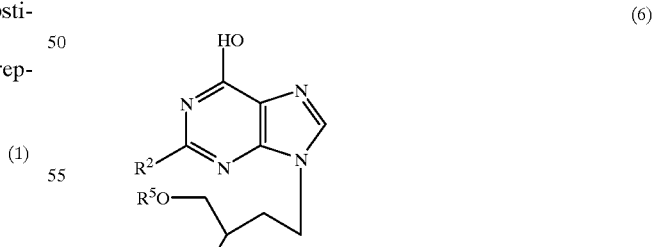

wherein
$R^2$ represents amino, $C_1-C_8$ mono- or diacylamino, $C_1-C_8$ alkoxycarbonylamino, or allyloxycarbonylamino, and
$R^5$ represents a $C_1-C_9$ acyl group, a $C_1-C_{10}$ alkyl group or $C_7-C_{22}$ aralkyl group.

DETAILED DESCRIPTION OF THE PREFERRED EMBODIMENTS

The compounds of formula (1) which are used in the present invention can be obtained from purine nucleosides having a saccharide chain in the 9-position or derivatives thereof. Specifically, 7-benzylguanine, 7-benzyladenine, 7-benzylhypoxanthine, 7-benzyl-2-aminopurine, 7-benzylxanthine and modified compounds thereof, which may have substituent introduced into the purine ring at another position except the 7-position are synthesized using guanosine, inosine, adenosine, 9-(β-D-ribofuranosyl)-2-aminopurine and the like as starting materials.

As to the benzyl group to be introduced into the 7-position, a substituent may be present on the phenyl ring of the benzyl group in any of the o-, m- and p-positions of the phenyl ring. Suitable substituents include methyl, nitro, methoxy, fluoro, chloro, bromo and iodo groups. The number of substituents may be one or more. Other examples of the substituents include benzyl, p-nitrobenzyl and p-methoxybenzyl groups.

The compound of formula (2) is a compound in which the leaving group is such as chlorine, bromine, iodine, p-toluenesulfonyloxy, mesyloxy, trifluoromethanesulfonyloxy, alkyl carbonate or phenyl carbonate, or $C_1$–$C_8$ saturated or unsaturated lower acyloxy group which is bound to a $C_1$–$C_{20}$ linear or branched saturated or unsaturated alkyl group which may have a 3- to 6-membered ring in the molecule and which may have an ether, thioether, acetal, thioacetal, lactone, thiolactone, ketone or amide structure in the molecule. Further, the above-mentioned $C_1$–$C_{20}$ linear or branched saturated or unsaturated-alkyl group may be substituted by hydroxyl, thiol sulfhydryl, $C_1$–$C_{20}$ alkoxy, $C_1$–$C_{10}$ acyl, $C_1$–$C_{10}$ acyloxy, carboxyl, $C_1$–$C_{10}$ alkoxycarbonyl, fluoro, chloro, bromo, iodo, amino, phosphoric acid, phosphonic acid, amino, protected by one or two protective groups selected from the group consisting of $C_1$–$C_8$ acyl, $C_1$–$C_8$ alkoxycarbonyl, allyloxycarbonyl, and a substituted phosphoric acid group and a substituted phosphonic acid group.

The $C_1$–$C_{22}$ linear or branched saturated or unsaturated alkyl group described supra is a side chain of nucleic acid derivatives containing a purine base, which has antiviral activity or antitumor activity, or their precursors. If the compound is as defined above, the reaction of the present invention proceeds smoothly. Therefore, it is not particularly limited.

Specifically, compounds having the following structures are examples of the compound of formula (2).

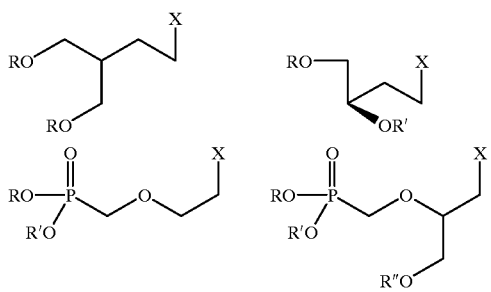

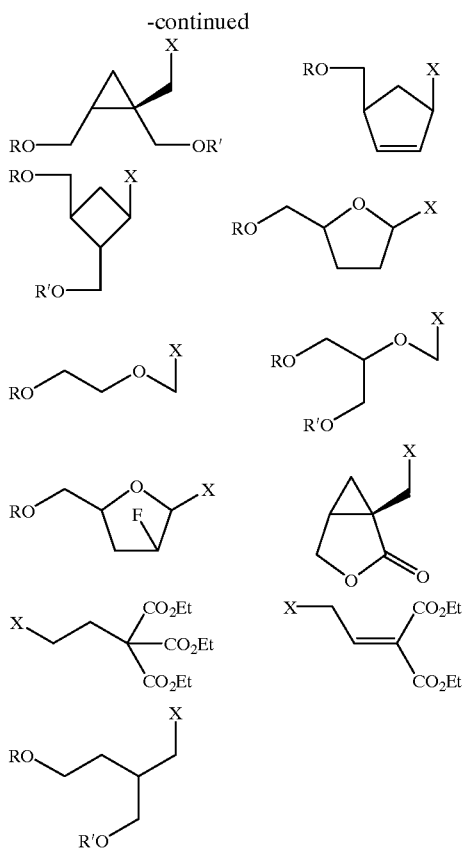

The above-mentioned compounds can be synthesized by the methods described in M. J. Robins et al., Can. J. Chem., 60, 547 (1982), EP 369583, WO 8910923, Harden et al., Tetrahedron Lett., 26(35), 4265 (1985), Harden et al., J. Mes. Chem., 30(9), 1636 (1987), Green et al., Tetrahedron Lett., 33(32), 4609 (1992), and H. C. Padgett, et al., J. Org. Chem., 44, 3492 (1979).

The compound of formula (3) which is a product and at the same time an intermediate is obtained by the reaction of the compound of formula (1) with the compound of formula (2).

The compound of formula (1) can be used in the form of a free substance or a salt such as hydrochloride or sulfate. Alternatively, the amino group which is a substituent in the purine base may be protected with a protective group for the amino group such as an acyl group, which is ordinarily used in synthesis of a nucleic acid.

The reaction is conducted in the presence or absence of a solvent. Examples of solvents include organic solvents such as dimethyl sulfoxide, N,N-dimethylformamide, N,N-dimethylacetamide; aromatic hydrocarbons such as toluene and xylene; ethers such as diethyl ether, diisopropyl ether and dioxane; alcohols such as methanol, ethanol and isopropyl alcohol; esters such as ethyl acetate, methyl acetate and isobutyl acetate; nitriles such as acetonitrile; ketones such as acetone, methyl ethyl ketone and methyl isobutyl ketone; and halogen compounds such as chloroform and dichloromethane. These solvents may be used either singly or in combination. When using dimethyl sulfoxide, N,N-dimethylformamide or N,N-dimethylacetamide, the reaction proceeds well in many cases because of the solubility of the purine base. The reaction may he conducted in the absence of a solvent.

The reaction is conducted usually at a temperature of from 0 to 200° C., preferably at a temperature of from 50 to 160° C. in view of working efficiency. The reaction is usually completed in from 0.5 to 48 hours. The reaction is conducted in the presence or absence of a solvent. The amount of the solvent employed is usually 1 g/deciliter or more, preferably 10 g/deciliter or more. The molar ratio of the compounds of formula (1) and (2) in the reaction is 1:1. In order to increase the yield of either of these compounds, an excessive amount of either of the compounds can be used.

The compounds of formula (3), which are obtained in the reaction of the present invention, are novel compounds except for the compounds of formula (3) in which $R^1$ is a hydroxyl group, $R^2$ is hydrogen or an amino group, $R^3$ is hydrogen and $R^4$ is a β-D-ribofuranosyl group. The known compounds are important intermediates in producing the desired compounds of the present invention. The compounds excluded from formula (3) can be synthesized by known procedures outside the process of the present invention. The compounds of the present invention, except for the excluded compounds, could have been easily synthesized by the process of the present invention for the first time.

The compound of formula (3) prepared by the process derived supra usually forms a salt with the anion ($X^-$) derived from the compound of formula (2) or a counter anion ($Y^-$) which is used in additives or during treatment as shown in formula (3').

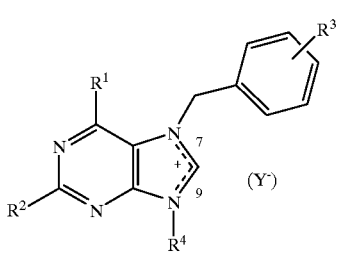

(3')

When compound (3') is isolated, the reaction solution is cooled, and a solvent such as ethyl acetate or chloroform is added thereto to precipitate the crystals which are then obtained by filtration. Alternatively, the reaction solution is extracted with a solvent, and then crystallized in a usual manner, after which the crystals are purified by silica-gel chromatography.

It is also possible that the compounds of formula (3), which are formed as salts with counter anion ($X^-$) or ($Y^-$), as shown in formula (3'), can be isolated and then reacted again with inorganic salts ($A^+Z^-$) to form salts with the desired counter anion ($Z^-$).

Examples of ($Y^-$) include $Br^-$ and $I^-$, and examples of the inorganic salts ($A^+Z^-$) include silver chloride ($Ag^+Cl^-$) and sodium perchlorate ($Na^+ClO_4^-$).

The compound of formula (3) can be debenzylated to eliminate the benzyl group or a substituted benzyl group, thereby resulting in the compound of formula (4).

The compound of formula (3), specifically, formula (3'), may be debenzylated as such or after the counter anion is replaced by another anion.

The benzyl group of the compound of formula (3) having the benzyl group or the likes of a p-nitrobenzyl group in the 7-position, can be eliminated by an ordinary method of removal of an N-benzyl group such as by reduction in the presence of a palladium catalyst under a hydrogen atmosphere, reduction in formic acid or formate in the presence of a palladium catalyst, or reduction using sodium or ammonia.

Examples of suitable palladium catalysts include palladium on active charcoal, palladium hydroxide, palladium black, a Lindlar catalyst, Pd—$CaCO_3$ and Pd—$BaCO_3$. The amount of the catalyst employed usually ranges from 1 and 10 mol % based on the substrate.

The hydrogen is normally employed at atmospheric pressure, but the reaction rate can be increased by increasing hydrogen pressure. The reaction is ordinarily carried out at a pressure of from 1 to 5 atm.

The substituted benzyl group that can be eliminated under acidic conditions or by exposure to light include 3,4-dimethoxybenzyl, o-nitrobenzyl, and di(p-methoxyphenyl)methyl, and the like.

Suitable solvents include water, N,N-dimethylformamide, N,N-dimethylacetamide; aromatic hydrocarbons such as toluene and xylene; ethers such as diethyl ether, diisopropyl ether and dioxane; alcohols such as methanol, ethanol and isopropyl alcohol; carboxylic acids such as acetic acid and propionic acid; esters such as ethyl acetate, methyl acetate and isobutyl acetate; nitrites such as acetonitrile and ketones such as acetone, methyl ethyl ketone and methyl isobutyl ketone. These solvents may be used either singly or in combination. When using N,N-dimethylformamide, N,N-dimethylacetamide, carboxylic acids such as acetic acid and propionic acid, and alcohols such as methanol, ethanol and isopropyl alcohol, the reaction proceeds smoothly in many cases in view of solubility.

The reaction is carried out usually at a temperature of from 0 to 200° C., preferably at a temperature of from 10 to 80° C. in view of working efficiency. The reaction is usually completed within 0.5 to 48 hours. The concentration of the solvent in the reaction is usually between 1 and 10 g/deciliter.

After the completion of the reaction, the catalyst is removed by filtration, and the solvent is concentrated if required, and a poor solvent is added or the extraction is conducted. Thus, the final compound can be isolated in the form of a free substance or as a salt by reaction with an acid. Examples of acids from which the salts can be formed include HCl, HBr and HI.

The present invention enables the selective production of purine derivatives having a substituent in the 9-position, which derivatives are quite useful as medicinal agents.

Having generally described this invention, a further understanding can be obtained by reference to certain specific examples which are provided herein for purposes of illustration only and are not intended to be limiting unless otherwise specified.

Synthesis Example 1

Guanosine (20.1 g, 62.7 mmol; water content 11.5%) was dissolved in 100 ml of dimethylsulfoxide. To this solution was added dropwise 20 ml (166 mmol) of benzyl bromide over a period of 20 min., and the mixture was stirred at room temperature for 22 h. After the completion of the reaction, 50 ml of conc. hydrochloric acid was added thereto, and the solution was poured into 600 ml of methanol. Further, 25 ml of conc. hydrochloric acid was added thereto, and the mixture was heated at 50° C. for 1 h. Then, the reaction mixture was allowed to cool with stirring for 3 h. The crystals precipitated were filtered, washed well with methanol, and then dried at 50° C. under reduced pressure for a yield of 17.4 g of 7-benzylguanine dihydrochloride (55.5 mmol; 88.5%).

$^1$H NMR (DMSO-d$_6$): δ8.90 (s, 1H), 7.45–7.29 (m, 5H), 5.52 (s, 2H).

ESI MS (MH$^+$): 242

Synthesis Example 2

Guanosine (10.0 g, 31.3 mmol; water content 11.5%) was dissolved in 50 ml of dimethylsulfoxide. To this solution was added dropwise 17.8 g (81.5 mmol) of 4-nitrobenzylbromide and the mixture was stirred at room temperature for 8 h. After the completion of the reaction, 25 ml of conc. hydrochloric acid and 100 ml of methanol were added thereto, and stirred at 50° C. for 4 h. Further, 200 ml of methanol was added thereto, and the mixture was stirred at room temperature for 1 h. The crystals precipitated were filtered, washed well with methanol, and then dried at 55° C. under reduced pressure for a yield of 8.8 g of 7-(4-nitrobenzyl)guanine dihydrochloride (24.6 mmol; 78.6%).

$^1$H NMR (DMSO-d$_6$): δ8.89 (s, 1H), 8.23 (d, 2H, J=8.7 Hz), 7.61 (d, 2H, J=8.8 Hz), 5.67 (s, 2H).

ESI MS (MH$^+$): 242

Synthesis Example 3

Guanosine (5.7 g; 20.0 mmol) was dissolved in 13.2 ml of dimethylsulfoxide. To this solution were added sodium iodide (0.6 g; 4 mmol) and 4-methoxybenzyl chloride (6.8 ml; 50.2 mmol), and the mixture was stirred at room temperature for 19 h. Conc. hydrochloric acid (10 ml) was added thereto, and stirred at 45° C. for 1 h. The mixture was cooled down to room temperature. Methanol (50 ml) was added thereto, and the mixture was stirred at room temperature for 3 h. The crystals precipitated were filtered, washed well with methanol (20 ml×3), and then dried at 50° C. under reduced pressure to obtain 2.5 g of 7-(4-methoxybenzyl) guanine dihydrochloride (34.8%).

$^1$H NMR (DMSO-d$_6$): δ8.87 (s, 1H), 7.41–6.91 (m, 4H), 7.28 (brs, 2H), 5.44 (s, 2H), 3.73 (s, 3H).

ESI MS (MH$^+$): 272

Synthesis Example 4

Inosine (11.0 g; 41.0 mmol) was dissolved in 50 ml of dimethylsulfoxide. To this was added dropwise 12.3 ml (102 mmol; 2.5 eq.) of benzyl bromide and the mixture was stirred at room temperature for 22.5 h. After the completion of the reaction, 40 ml of conc. hydrochloric acid was added thereto, and stirred at 45–50° C. for 3.5 h. The reaction mixture was cooled to 5° C., and then, neutralized by 82 ml of 20% aq. NaOH. Water (200 ml) was added thereto, and stirred at room temperature overnight. The precipitated crystals were filtered, washed well with 100 ml of water and 50 ml of diethylether, then dried at 50° C. under reduced pressure for a yield of 7.84 g of 7-benzylhypoxanthine (34.7 mmol; 84.5%).

$^1$H NMR (DMSO-d$_6$): δ12.32 (brs, 1H), 8.39 (s, 1H, H-2), 7.97 (brd, 1H), 7.40–7.25 (m, 5H), 5.56 (s, 2H)

EXAMPLE 1

Acetic anhydride (4.44 ml; 45.1 mmol) and 132.8 mg (0.698 mmol) of p-toluenesulfonic acid monohydrate were added to a mixed solution containing 4.37 g (13.9 mmol) of 7-benzylguanine dihydrochloride and 9 ml of acetic acid. The mixture was heated at 105° C. for 3 h, and then allowed to cool. Water (180 ml) was added to the reaction solution, and 150 ml of 5% sodium bicarbonate and 100 ml of 1N sodium hydroxide were added thereto to adjust the pH to 5.3. Then, the crystals were filtered, washed with 50 ml of water, and dried at 55° C. under reduced pressure for 5 h for a yield of 3.77 g (13.3 mmol; 95.7%) of N$^2$-acetyl-7-benzylguanine as a white solid.

$^1$H NMR (DMSO-d$_6$): δ12.10 (brs, 1H), 11.57 (s, 1H) 8.35 (s, 1H), 7.41–7.25 (m, SH), 5.51 (s, 2H), 2.16 (s, 3H).

EXAMPLE 2

4-Dimethylaminopyridine (145.6 mg; 1.19 mmol) and benzoylchloride (5.5 ml; 47.4 mmol) were added to a mixed solution containing 7.29 g (23.7 mmol) of 7-benzylguanine dihydrochloride and 47 ml of pyridine. The mixture was heated at 96° C. for 2 h, and then allowed to cool. Ethyl acetate (95 ml) was added to the reaction solution, and stirred at room temperature for 30 min. Then, the crystals were filtered, stirred with 95 ml of water, filtered again and washed well with water. The product was dried at 50° C. under reduced pressure for 15 h for a yield of 7.79 g of N$^2$-benzoyl-7-benzylguanine as a white solid (22.6 mmol; 96%).

$^1$H NMR (DMSO-d$_6$): δ12.37 (brs, 1H), 11.87 (brs, 1H), 8.39 (s, 1H), 8.08–8.03 (m, 2H), 7.70–7.52 (m, 3H), 7.41–7.26 (m, 5H), 5.55 (s, 2H).

ESI MS (MH$^+$): 346

EXAMPLE 3

Acetic anhydride (4.80 ml; 49.3 mmol) and 145.8 mg (0.766 mmol) of p-toluenesulfonic acid monohydrate were added to a mixed solution containing 5.40 g (15.03 mmol) of 7-(4-nitrobenzyl)guanine dihydrochloride and 10 ml of acetic acid. The mixture was heated at 107° C. for 3.5 h, and acetic anhydride (4.80 ml) and acetic acid (10 ml) were added again. After the reaction for 8 h, the reaction mixture was allowed to cool, and concentrated under reduced pressure. By adding water (150 ml) and 2N NaOH (106 ml) to the concentrate, pH was adjusted to 6. The crystals obtained were filtered, washed with 134 ml of water and dried at 50° C. under reduced pressure for a yield of 4.97 g of N$^2$-acetyl-7-(4-nitrobenzyl)guanine as a white solid (15.0 mmol; 100%).

$^1$H NMR (DMSO-d$_6$): δ12.10 (brs, 1H), 11.60 (brs, 1H), 8.40 (s, 1H), 8.21 (d, 2H, J=8.9 Hz), 7.54 (d, 2H, J=8.9 Hz), 5.67 (s, 2H), 2.16 (s, 3H).

EXAMPLE 4

4-Bromobutyl acetate (0.776 ml; content 98%; 5.25 mmol; 1.05 eq.) was added to a mixed solution containing 1.42 g (5.00 mmol) of N$^2$-acetyl-7-benzylguanine and 5 ml of DMF. The mixture was heated at 75° C. for 20 h, and then allowed to cool. Ethyl acetate (20 ml) was added thereto, and the mixture was stirred at room temperature (25° C.). A precipitated solid was filtered, washed with ethyl acetate and then dried at 50° C. under reduced pressure for a yield of 1.86 g of 9-(4-acetoxybutyl)-N$^2$-acetyl-7-benzylguaninium bromide as a white solid (3.90 mmols; 77.9%).

$^1$H NMR (DMSO-d$_6$): δ12.60 (brs, 1H), 12.16 (s, 1H), 9.86 (s, 1H), 7.53–7.36 (m, 5H), 5.71 (s, 2H), 4.28 (t, 2H, J=7.2 Hz), 4.04 (t, 2H, J=6.5 Hz), 2.23 (s, 3H), 2.01 (s, 3H), 1.99–1.88 (m, 2H), 1.69–1.59 (m, 2H).

FAB MS (M$^+$): 398

Anal. Calcd for C$_{29}$H$_{24}$N$_6$O$_4$Br: C, 50.2; H, 5.1; N, 14.6. Found: C, 50.3; H, 5.1; N, 14.7.

EXAMPLE 5

4-Bromobutyl acetate (0.78 ml; content 98%; 5.28 mmol; 1.05 eq.) was added to a mixed solution containing 1.42 g (5.02 mmol) of $N^2$-acetyl-7-benzylguanine and 2.5 ml of DMF. The mixture was heated at 85° C. for 20 h, and then allowed to cool. Ethyl acetate (10 ml) was added thereto, and the mixture was stirred at room temperature. A white precipitate was filtered, washed with ethyl acetate, and then dried at 50° C. under reduced pressure for a yield of 2.09 g of 9-(4-acetoxybutyl)-$N^2$-acetyl-7-benzylguaninium bromide as a white solid (4.38 mmol; 86.4%).

EXAMPLE 6

4-Bromobutyl acetate (6.12 ml; content 98%, 41.4 mmol; 1.05 eq.) was added to a mixed solution containing 12.2 g (39.5 mmol; content 92%) of $N^2$-acetyl-7-benzylguanine and 20 ml of DMF. The mixture was heated at 85° C. for 19.5 h, and then 1.14 ml of 4-bromobutyl acetate was added and heated at 90° C. for 12 h, then allowed to cool. Ethyl acetate (80 ml) was added thereto, and the mixture was stirred at room temperature. A white precipitate was filtered, washed with ethyl acetate, and then dried under reduced pressure for a yield of 16.9 g of 9-(4-acetoxybutyl)-$N^2$-acetyl-7-benzylguaninium bromide as a white solid (35.4 mmol; 89.5%).

EXAMPLE 7

4-Iodobutyl acetate (0.187 ml; content 85%; 1.06 mmol; 1.05 eq.) was added to a mixed solution containing 284.7 mg (1.01 mmol) of $N^2$-acetyl-7-benzylguanine and 2 ml of DMF. The mixture was heated at 80° C. for 20 h, and then allowed to cool. To this solution was added 10 ml of chloroform, and the precipitated crystals were collected by filtration, and dried at 50° C. for 3 h under reduced pressure for a yield of 265.7 mg of 9-(4-acetoxybutyl)-$N^2$-acetyl-7-benzylguaninium iodide as a pale purple solid (50.3%). Further, the filtrate was concentrated under reduced pressure, and the residue was purified by silica-gel column chromatography (Chloroform/methanol at a ratio of 20/1 to 15/1) for a yield of 138.0 mg of the above-mentioned product (26.1%).

$^1$H NMR (DMSO-$d_6$): δ12.60 (brs, 1H), 12.15 (s, 1H), 9.70 (s, 1H), 7.51–7.39 (m, 5H), 5.69 (s, 2H), 4.27 (t, 2H, J=7.2 Hz), 4.04 (t, 2H, J=6.5 Hz), 2.22 (s, 3H), 2.00 (s, 3H), 1.97–1.87 (m, 2H), 1.68–1.59 (m, 2H).

FAB MS (M$^+$) 398

Anal. Calcd for $C_{29}H_{24}N_6O_4I$: C, 45.7; H, 4.6; N, 13.3. Found: C, 45.7; H, 4.8; N, 13.6.

EXAMPLE 8

4-Bromobutyl acetate (2.76 ml; content 98%; 18.7 mmol; 1.2 eq.) was added to a mixed solution containing 5.37 g (15.6 mmol) of $N^2$-benzoyl-7-benzylguanine and 10 ml of DMF. The mixture was heated at 80° C. for 21.5 h, and then allowed to cool. Ethyl acetate (48 ml) was added thereto, and the mixture was stirred at room temperature. A white precipitate was filtered, washed with ethyl acetate, and then dried at 50° C. under reduced pressure for a yield of 6.02 g of 9-(4-acetoxybutyl)-$N^2$-benzoyl-7-benzylguaninium bromide as a pale brown solid (71.6%).

$^1$H NMR (DMSO-$d_6$): δ12.92 (brs, 1H), 12.31 (s, 1H), 9.78 (s, 1H), 8.09–8.02 (m, 2H), 7.75–7.35 (m, 3H), 5.73 (s, 2H), 4.31 (t, 2H, J=7.2 Hz), 4.05 (t, 2H, J=6.4 Hz), 2.00 (s, 3H), 2.07–1.90 (m, 2H), 1.72–1.60 (m, 2H).

FAB MS (M$^+$) 460.4

EXAMPLE 9

2-Acetoxymethyl-4-bromobut-1-yl acetate (7.48 g; 28.0 mmol; 1.1 eq.) was added to a mixed solution containing 8.79 g (25.4 mmol) of $N^2$-benzoyl-7-benzylguanine and 21 ml of DMF. The mixture was heated at 90° C. for 18.5 h, and then allowed to cool. Ethyl acetate (85 ml) was added thereto, and the mixture was stirred at room temperature. A white precipitate was filtered, washed with ethyl acetate, and then dried at 50° C. under reduced pressure for a yield of 10.86 g of 9-(4-acetoxy-3-acetoxymethylbut-1-yl)-$N^2$-benzoyl-7-benzylguaninium bromide as a white solid (17.7 mmol; 69.6%).

$^1$H NMR (DMSO-$d_6$): δ9.79 (s, 1H), 8.07–8.02 (m, 2H), 7.75–7.38 (m, 8H) 5.73 (s, 2H), 4.38 (t, 2H, J=7.2 Hz), 4.07 (d, 4H, J=5.6 Hz), 2.02 (s, 6H), 2.15–1.94 (m, 3H)

ESI MS (M$^+$) 532

EXAMPLE 10

4-Bromobutyl acetate (0.31 ml; content 98%; 2.07 mmol; 1.05 eq.) was added to a mixed solution containing 673 mg (1.98 mmol; content 96%) of $N^2$-acetyl-7-(4-nitrobenzyl) guanine and 2 ml of DMF. The mixture was heated at 84° C. for 40 h, and then allowed to cool. Chloroform (6 ml) was added thereto, and the mixture was stirred at room temperature. A precipitate was filtered, washed with chloroform, and then dried at 50° C. under reduced pressure to recover $N^2$-acetyl-7-(4-nitrobenzyl)guanine. From the filtrate standing overnight, a precipitate was again obtained. Ethyl acetate (10 ml) was added thereto, and the mixture was stirred at room temperature. The precipitate was filtered, washed with ethyl acetate, and then dried at 50° C. under reduced pressure for a yield of 819 mg of 9-acetoxybutyl-$N^2$-acetyl-7-(4-nitrobenzyl)guaninium bromide as a solid (1.56 mmol; 79.0%).

$^1$H NMR (DMSO-$d_6$): δ12.17 (s, 1H), 9.81 (s, 1H), 8.29–8.24 (m, 2H), 7.77–7.70 (m, 2H), 5.85 (s, 2H), 4.29 (t, 2H, J=7.2 Hz), 4.05 (t, 2 H, J=6.5 Hz), 2.22 (s, 3H), 2.01 (s, 3H), 1.98–1.87 (m, 2H), 1.72–1.60 (m, 2H).

FAB MS (M$^+$) 443

EXAMPLE 11

9-(4-Acetoxybutyl)-$N^2$-acetyl-7-benzylguaninium bromide (124 mg) was added to a mixed solution containing DMF (5 ml) and acetic acid (5 ml), 116 mg of 5% Pd/C (water content 52.9%; 10 mol %) and 13.4 mg of 20% Pd(OH)$_2$/C (10 mol %). The reaction was carried out at a temperature of from room temperature to 60° C. under hydrogen atmosphere (1 atm) To complete the reaction, the reduction was further conducted at room temperature under hydrogen pressure of 3 atm for 14 h. After the completion of the reaction, the reaction mixture was filtered through Celite, and the solvent was removed by distillation under reduced pressure. Then, the residue was washed with ethyl acetate. The precipitated crystals were filtered for a yield of 75.3 mg of 9-(4-acetoxybutyl)-$N^2$-acetylguanine hydrobromide as a white solid (74.9%).

$^1$H NMR (DMSO-$d_6$): δ8.00 (s, 1H), 4.08 (t, 2H, J=7.1 Hz), 4.00 (t, 2H, J=6.6 Hz), 2.18 (s, 3H), 1.99 (s, 3H), 1.87–1.77 (m, 2H), 1.59–1.49 (m, 2H)

FAB MS (M$^+$) 308

EXAMPLE 12

To a mixed solution containing 125 mg (0.262 mmol) of 9-(4-acetoxybutyl)-$N^2$-acetyl-7-benzylguaninium bromide and 2.6 ml of acetic acid was added 59.9 mg (water content 52.9%; 5 mmol%) of 5% Pd/C. Catalytic reduction was carried out by heating the mixture at 60° C. under a hydrogen atmosphere. After 5.5 h, the reaction was completed, and the reaction mixture was filtered through Celite. The filtrate was analyzed by HPLC. It was confirmed that 83.7 mg of 9-(4-acetoxybutyl)-$N^2$-acetylguanine hydrobromide was produced (0.216 mmol; 82.3%).

EXAMPLE 13

To a mixed solution containing 485 mg (1.01 mmol) of 9-(4-acetoxybutyl)-$N^2$-acetyl-7-benzylguaninium bromide and 10 ml of dimethylformamide was added 227 mg (water content 52.9%; 5 mmol %) of 5% Pd/C. Catalytic reduction was conducted at room temperature (26° C.) under a hydrogen atmosphere of 2.9 atm for 3 h. Then, the reaction temperature was elevated to 38° C., and the reaction was conducted for 22 h. After the completion of the reaction, the reaction mixture was filtered through Celite. The filtrate was analyzed by HPLC. It was confirmed that 290 mg of 9-(4-acetoxybutyl)-$N^2$-acetylguanine hydrobromide was produced (0.746 mmol; 73.6%).

EXAMPLE 14

To a mixed solution containing 733 mg (1.53 mmol) of 9-(4-acetoxybutyl)-$N^2$-acetyl-7-benzylguaninium bromide and 7.7 ml of acetonitrile was added 352 mg of 5% Pd/C (water content 54%; 5 mmol %). Catalytic reduction was conducted at 55° C. under a hydrogen atmosphere of 1 atm for 2.5 h. After completion of the reaction, the reaction mixture was analyzed by HPLC and it was confirmed that 9-(4-acetoxybutyl)-$N^2$-acetylguanine was obtained in quantitative yield.

EXAMPLE 15

9-(4-Acetoxybutyl)-$N^2$-acetyl-7-benzylguaninium bromide (39.7 g; content 97.5%; 80.8 mmol) was added to a mixed solution of methanol (404 ml) and 7.48 g (1.62 mmol) of 5% Pd/C (water content 54%). The reaction was carried out at 50° C. for 4 h under hydrogen atmosphere (1 atm). After completion of the reaction (confirmed by HPLC), the reaction mixture was filtered through Celite, and the solvent was removed by distillation under reduced pressure. Then, water (130 ml) and 25% NaOH (45.2 g) were added to the residue and stirred overnight at 40° C. The mixture was neutralized by 2N HCl stirred at room temperature for 2 h. The precipitated crystals were filtered and dried at 50° C. under reduced pressure for a yield of 17.33 g of 9-hydroxybutylguanine (97.2% purity, 93.4% yield).

$^1$H NMR (DMSO-$d_6$): δ7.68 (s, 1H), 6.45 (brs, 2H), 4.45 (t, 1H), 3.93 (t, 2H), 3.40 (m, 2H), 1.74 (m, 2H), 1.37 (m, 2H)

EXAMPLE 16

9-(4-Acetoxy-3-acetoxymethylbut-1-yl)-$N^2$-benzoyl-7-benzylguaninium bromide (8.91 g; 14.5 mmol) and 5% Pd/C (3.30 g; water content 53.5%; 0.73 mmol) in ethanol (36.5 ml) were stirred at 50° C. for 3.5 h under a hydrogen atmosphere (1 atm). After the completion of the reaction, the reaction mixture was filtered through Celite, and the solvent was removed by distillation under reduced pressure. Then, water (15 ml) and 25% NaOH (21 g) were added to the residue and stirred at 65° C. for 2 h. The mixture was cooled by an ice bath and neutralized by the addition of 6N HCl (14.5 ml). The precipitated crystals were filtered, washed with water and dried at 60° C. under reduced pressure for a yield of 2.73 g of 9-(4-hydroxy-3-hydroxymethylbut-1-yl)guanine (Penciclovir) (67.3%).

$^1$H NMR (DMSO-$d_6$): δ10.52 (brs, 1H), 7.68 (s, 1H), 6.42 (s, 2H), 4.42 (t, 2H, J=5.1 Hz), 3.99 (dd, 2H, J=6.8, 7.8 Hz), 3.47–3.29 (m, 4H), 1.70 (dt, 2H, J=6.9, 7.9 Hz), 1.50–1.39 (m, 1H).

ESI MS (MH$^+$) 254.1

EXAMPLE 17

4-Bromobutyl acetate (4.45 ml; content 98%; 30.1 mmol; 1.2 eq.) was added to a mixed solution containing 5.67 g (25.1 mmol) of 7-benzylhypoxanthine and 12.5 ml of DMF. The mixture was heated at 76° C. for 21 h, and then allowed to cool. Ethyl acetate (62.5 ml) was added thereto, and the mixture was stirred at room temperature. A precipitate was filtered, washed with ethyl acetate (9 ml), and then dried under reduced pressure for a yield of 4.40 g of 9-acetoxybutyl-7-benzylhypoxanthinium bromide as white crystals (9.77 mmol; 38.9%).

$^1$H NMR (DMSO-$d_6$): δ9.83 (s, 1H), 8.42 (s, 1H), 7.53–7.34 (m, 5H), 5.74 (s, 2H), 4.36 (t, 2H, J=7.2 Hz), 4.03 (t, 2H, J=6.5 Hz), 2.00 (s, 3H), 2.04–1.87 (m, 2H), 1.69–1.57 (m, 2H).

ESI MS (M$^+$) 341.3

EXAMPLE 18

9-Acetoxybutyl-7-benzylhypoxanthinium bromide (679 mg; Content 93.5%; 1.51 mmol) and 5% Pd/C (345 mg; water content 54%; 5 mol %) in methanol (7.5 ml) were stirred at 45° C. for 5.5 h under hydrogen atmosphere (1 atm). After the completion of the reaction, the reaction mixture was filtered through Celite, and the solvent was removed by distillation under reduced pressure. 1N NaOH (3 ml) was added to the concentrate and stirred overnight, then 1N NaOH (1.5 ml) was added again and stirred for an additional 2 h. The mixture was neutralized by the addition of 2N HCl and purified by column chromatography (Synthetic adsorption resin; water-50% MeOH) for a yield of 254 mg of 9-hydroxybutylhypoxanthine as white crystals (81.0%).

$^1$H NMR (DMSO-$d_6$): δ8.09 (s, 1H), 8.03 (s, 1H), 4.14 (t, 2H, J=7.1 Hz), 3.39 (t, 2H, J=6.4 Hz), 1.88–1.76 (m, 2H), 1.43–1.31 (m, 2H)

ESI MS (MH$^+$) 209.2

EXAMPLE 19

Acetic anhydride (3.54 ml; 37.5 mmol) and 95 mg (0.5 mmol) of p-toluenesulfonic acid monohydrate were added to a mixed solution containing 1.7 g (4.9 mmol) of 7-(4-methoxybenzyl)guanine dihydrochloride and 10 ml of acetic acid. The mixture was heated at 100° C. for 5 h, and then allowed to cool. Water (20 ml) was added to the reaction solution, and 2N sodium hydroxide was added thereto to adjust the pH to 2. Then, the crystals were filtered, washed with 10 ml of water two times, and 20 ml of water was added again. 2N sodium hydroxide was added thereto to adjust the pH to 6 and the crystals were filtered, washed with 10 ml of water and dried at 50° C. under reduced pressure for 5 h for a yield of 1.29 of $N^2$-acetyl-7-(4-methoxybenzyl)guanine (76.8%).

$^1$H NMR (DMSO-$d_6$): δ8.32 (s, 1H), 7.36–6.88 (m, 4H), 5.42 (s, 2H), 3.71 (s, 3H), 2.15 (s, 3H).

ESI MS (MH$^+$): 314

EXAMPLE 20

4-Bromobutyl acetate (0.33 ml, content 98%, 2.2 mmol) was added to a mixed solution containing 630 mg (1.8 mmol, content 91%) of $N^2$-acetyl-7-(4-methoxybenzyl)guanine and 2 ml of DMF. The mixture was heated at 50° C. for 18 h and at 80° C. for 24 h, and then allowed to cool. 2-Propanol (8 ml) was added thereto, and the mixture was stirred at room temperature for 1 h. A precipitate was filtered and then dried at 50° C. under reduced pressure to recover starting $N^2$-acetyl-7-(4-methoxybenzyl)guanine (0.14 g). The filtrate was concentrated and purified by column chromatography ($CHCl_3$/MeOH 95/5). The fractions containing the product were concentrated and 5 ml of 2-propanol was added thereto. The crystals were filtered, washed with 2-propanol and dried at 50° C. under reduced pressure for a yield of 0.29 g of 9-acetoxybutyl-$N^2$-acetyl-7-(4methoxybenzyl)guaninium bromide as a white solid.

$^1$H NMR (DMSO-$d_6$): δ7.49–6.96 (m, 4H), 5.61 (s, 2H), 4.26–4.21 (t, 2H), 4.03 (t, 2H, J=6.5 Hz), 3.75 (s, 3H), 2.22 (s, 3H), 2.00 (s, 3H), 1.97–1.83 (m, 2H), 1.68–1.56 (m, 2H).

ESI MS ($M^+$): 428

EXAMPLE 21

To a mixed solution containing 100 mg (0.35 mmol) of $N^2$-acetyl-7-benzylquanine and 1 ml of DMF was added 72 mg (0.37 mmol) of (2-acetoxyethoxy)methyl bromide [prepared by the method described in M. J. Robins et al., Can. J. Chem., 60, 547 (1982)]. The mixture was heated at 80° C. for 20 h, and then allowed to cool. The reaction solution was concentrated, and purified by silica-gel column chromatography to yield 9-(2-acetoxyethoxy)methyl-7-benzyl-$N^2$-acetylguaninium bromide.

$^1$H NMR (DMSO-$d_6$): δ9.70 (s, 1H), 7.55–7.33 (m, 5H), 7.10 (s, 2H), 5.69 (d, 2H, J=13.5 Hz), 4.12 (m, 2H), 3.86 (m, 2H), 2.22 (s, 3H), 1.94 (s, 3H)

FAB MS ($M^+$): 400

EXAMPLE 22

To a mixed solution containing 100 mg (0.35 mmol) of $N^2$-acetyl-7-benzylquanine and 1 ml of DMF was added 64 mg (0.37 mmol) of (2-acetoxyethoxy)methyl acetate [prepared by the method described in M. J. Robins et al., Can. J. Chem., 60, 547 (1982)]. The mixture was heated at 80° C. for 20 h, and then allowed to cool. The reaction solution was concentrated, and purified by silica-gel column chromatography to yield 9-(2-acetoxyethoxy)methyl-7-benzyl-$N^2$-acetylguaninium acetate.

EXAMPLE 23

To a mixed solution containing 206 mg (0.79 mmol) of $N^2$-acetyl-7-benzylguanine and 1.5 ml of DMF was added 150 mg (0.79 mmol) of (3-oxa-2-oxobicyclo[3.1.0]hexan-1-yl)methyl bromide (obtained by reacting mesylate described in Japanese Patent Application No. 61,250/1994). The mixture was reacted at 80° C. for 25.5 h, and then allowed to cool. Ethyl acetate (30 ml) was added to the reaction solution, and the mixture was stirred at room temperature for 10 min. The precipitated crystals were then collected by filtration, washed with 5 ml of ethyl acetate, and dried to obtain 9-(3-oxa-2-oxobicyclo[3.1.0]hexan-1-yl)methyl-7-benzyl-$N^2$-acetylguaninium bromide.

$^1$H NMR (DMSO-$d_6$): δ12.10 (s, 1H), 9.39 (s, 1H), 7.60–7.35 (m, 5H), 5.74 (s, 2H), 4.87 (d, 2H, J=11.3 Hz), 4.66 (d, 2H, J=11.3 Hz), 4.32 (m, 1H), 4.12 (m, 1H), 2.49 (s, 3H), 2.08 (m, 1H), 1.28 (t, 1H, J=5.1 Hz), 1.10 (m, 1H).

FAB MS ($M^+$): 394

Effect of the Invention

Purine derivatives having a substituent in the 9-position, which are useful as medicinal agents, can be synthesized selectively.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound represented by formula (3):

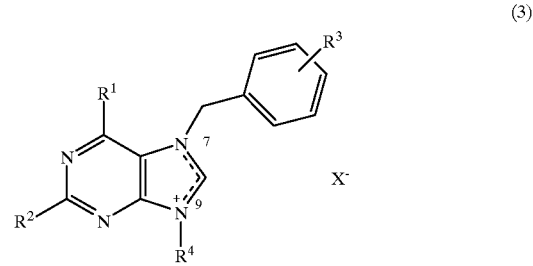

wherein:

$R^1$ is hydrogen, hydroxyl, $C_1$–$C_8$ saturated or unsaturated alkoxy, $C_1$–$C_8$ saturated or unsaturated hydrocarbon acyloxy, fluoro, chloro, bromo, iodo, $C_1$–$C_8$ mono- or di-hydrocarbon acylamino, $C_1$–$C_8$ alkoxycarbonylamino, allyloxycarbonylamino, or $C_1$–$C_8$ saturated or unsaturated alkyl;

$R^2$ is hydrogen, hydroxyl, $C_1$–$C_8$ saturated or unsaturated alkoxy, $C_1$–$C_8$ saturated or unsaturated hydrocarbon acyloxy, fluoro, chloro, bromo, iodo, amino, $C_1$–$C_8$ mono- or di-hydrocarbonacylamino, $C_1$–$C_8$ alkoxycarbonylamino, allyloxycarbonylamino, or $C_1$–$C_8$ saturated or unsaturated alkyl;

$R^3$ is hydrogen, $C_1$–$C_6$ alkyl, $C_1$–$C_6$ alkoxy, hydroxyl, nitro, amino, carboxyl, $C_1$–$C_6$-alkoxycarbonyl, fluoro, chloro, bromo or iodo;

$R^4$ is a $C_1$–$C_{20}$ linear or branched, saturated or unsaturated alkyl, a $C_1$–$C_{20}$ linear or branched, saturated or unsaturated alkyl substituted by a $C_{3-6}$ carbocyclic ring, or a $C_1$–$C_{20}$ linear or branched, saturated or unsaturated alkyl substituted by at least one hydroxy, sulfhydryl, $C_{1-20}$-alkoxy, $C_1$–$C_{10}$-saturated or unsaturated hydrocarbon acyl, $C_1$–$C_{10}$-saturated or unsaturated hydrocarbon acyloxy, carboxy, —P(O)(OH)$_2$, —O—P(O)(OH)$_2$, $C_{1-8}$-mono- or di-hydrocarbonacylamino, $C_{1-8}$-alkoxycarbonylamino or allyloxycarbonylamino group; and $X^-$ represents chloride, bromide, iodide, p-toluenesulfonate, methanesulfonate, trifluoromethanesulfonate, alkyl carbonate or phenyl carbonate, or saturated or unsaturated hydrocarbon carboxylate having 1–8 carbon atoms.

* * * * *

UNITED STATES PATENT AND TRADEMARK OFFICE
CERTIFICATE OF CORRECTION

PATENT NO.    : 6,245,910 B1　　　　　　　　　　　　　　　　　　　Page 1 of 1
DATED         : June 12, 2001
INVENTOR(S)   : Kunisuke Izawa et al.

It is certified that error appears in the above-identified patent and that said Letters Patent is hereby corrected as shown below:

Column 6,
Line 30, "amino, $C_1$—$C_9$ mono-" should read -- amino, $C_1$—$C_8$ mono- --;
Line 44, "a $C_1$—$C_9$ acyl group," should read -- a $C_1$—$C_8$ acyl group, --;
Line 66, "a $C_1$—$C_9$ acyl group," should read -- a $C_1$—$C_8$ acyl group, --;

Signed and Sealed this

Fifth Day of March, 2002

Attest:

JAMES E. ROGAN
Attesting Officer　　　Director of the United States Patent and Trademark Office